United States Patent
Foerster et al.

(10) Patent No.: US 7,993,001 B2
(45) Date of Patent: Aug. 9, 2011

(54) DIAPHANOSCOPE ROD

(75) Inventors: Michael Foerster, Berlin (DE);
Nikolaos Bechrakis, Berlin (DE);
Dieter Mann, Kleinwallstadt (DE)

(73) Assignee: Dieter Mann GmbH, Mainaschaff (DE)

( * ) Notice: Subject to any disclaimer, the term of this patent is extended or adjusted under 35 U.S.C. 154(b) by 0 days.

(21) Appl. No.: 12/532,607

(22) PCT Filed: Mar. 20, 2008

(86) PCT No.: PCT/EP2008/002294
§ 371 (c)(1),
(2), (4) Date: Sep. 22, 2009

(87) PCT Pub. No.: WO2008/116609
PCT Pub. Date: Oct. 2, 2008

(65) Prior Publication Data
US 2010/0118271 A1 May 13, 2010

(30) Foreign Application Priority Data

Mar. 23, 2007 (DE) .......................... 10 2007 014 703

(51) Int. Cl.
*A61B 3/10* (2006.01)

(52) U.S. Cl. ........................................................ 351/221
(58) Field of Classification Search ................ 351/200, 351/205, 213, 216, 221
See application file for complete search history.

(56) References Cited

U.S. PATENT DOCUMENTS

| | | | |
|---|---|---|---|
| 2,660,732 A | 12/1953 | Stone, Jr. | |
| 5,335,648 A | 8/1994 | Kozawa et al. | |
| 5,822,036 A * | 10/1998 | Massie et al. | 351/219 |
| 6,196,686 B1 * | 3/2001 | Reiner | 351/221 |

FOREIGN PATENT DOCUMENTS

| | | |
|---|---|---|
| DE | 1952119 U | 12/1966 |
| DE | 86949 | 1/1972 |
| DE | 4302614 A1 | 8/1993 |
| EP | 0432692 A1 | 6/1991 |
| EP | 0651981 A1 | 5/1995 |
| SU | 1780502 A3 | 12/1992 |

* cited by examiner

*Primary Examiner* — Huy K Mai
(74) *Attorney, Agent, or Firm* — McDonnell Boehnen Hulbert & Berghoff LLP

(57) ABSTRACT

A diaphanoscope rod that comprises a rod having a first end and a second end, that is made of a transparent or translucent material, and also a light feeding device. According to the invention, one end of the rod comprises a light deflecting device.

15 Claims, 1 Drawing Sheet

DIAPHANOSCOPE ROD

The present invention refers to a diaphanoscope rod.

During the method of diaphanoscopy the eye is X-rayed by a direct light source put on the eye. It serves to identify light absorbing structures in the inside of the eye such as tumors, bleedings or foreign bodies, which cause shadows during the diaphanoscopy.

A known diaphanoscope rod comprises a metal pipe in which light-guiding fibers are embedded. The light rod generates a punctual light which can be seen ophthalmologically. Hereby a binocular indirect ophthalmoscope is usually used. However, the light spot is too small for carrying out the evaluation of the position of a tantalum clip with respect to a tumor. Furthermore, the applied light intensity is insufficient for a substantiated diagnosis.

The light conduction is usually carried out by a fiber optic cable. The light fiber is the basic element of all fiber optic parts. It comprises a highly refracting glass core and a lowly refracting glass cladding. Beams of light which enter on the front side of the fibers are guided within the core along the bounding surface core/cladding by total reflection and follow all curvings of the fiber for leaving the fiber at the end. The numeric aperture, the optical transmissibility and the diameter of the fibers are the most important characteristics of light guiding fibers.

It is the object of the present invention to provide a diaphanoscope rod with improved light power.

The object to provide an improved diaphanoscope rod is solved by the subject-matter of the invention according to patent claim 1. Further developments of the invention are given in the dependent claims.

The diaphanoscope rod according to the invention furthermore has the advantage that it allows the monitoring of the position of a tantalum clip which is sewed on the outside of the eye referring to a tumor which is located in the inside of the eye. This also determines the form of the diaphanoscope rod. The monitoring of the position is necessary, since at a later time, it determines the coordinates for the irradiation of the tumor. The light conduction of the diaphanoscope rod is based on total reflection.

Figure 1:
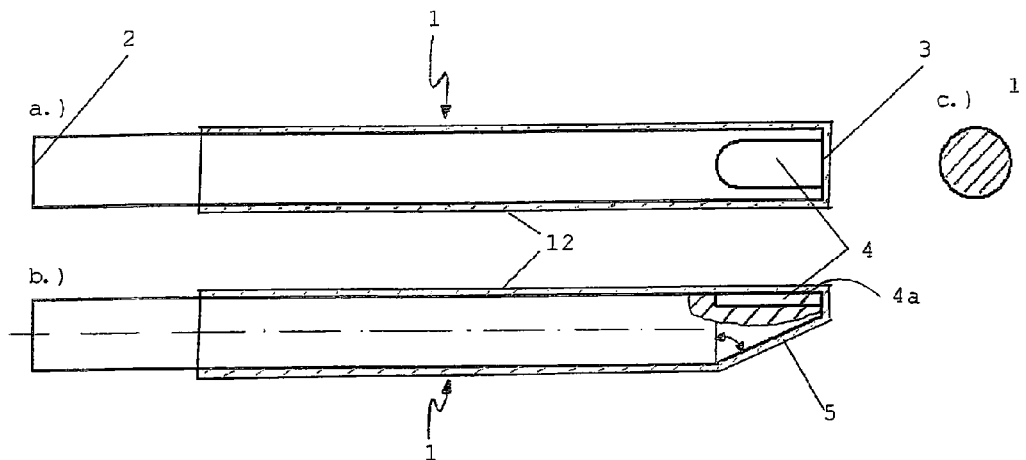
Figure 2:
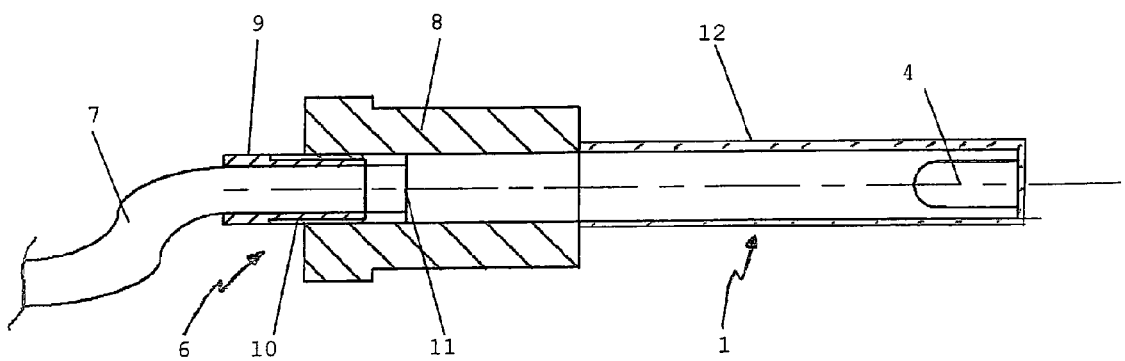

Further features and advantages of the invention will become apparent from the description of embodiments by reference to the accompanying drawings. The figures show:

FIG. 1a a top view on the diaphanoscope rod;

FIG. 1b a longitudinal section of the diaphanoscope rod;

FIG. 1c a section of the diaphanoscope rod perpendicular to the rod axis;

FIG. 2 a local section of the diaphanoscope rod having a light feeding device.

As shown in FIGS. 1a-1c and 2, the diaphanoscope rod comprises a rod 1 having a first end 2 and a second end 3, wherein at the first end 2 a light feeding device 6 is provided and at the second end 3 a recess 4 e.g. for a tantalum clip, and a light deflecting device 5 is provided.

The rod 1 preferably has a circular or a square cross-section and can have any length the operator desires. It is made of translucent material, for example glass or plastics. All transparent and translucent plastics or glass types can be used. The material presently used is an optical glass which is free of inclusions as far as possible and which lets pass a large spectrum of wavelengths. The glass is drawn out to the appropriate cross-section string and therefore has a very good surface quality and also can stand high stresses. The choice of the diameter of the rod 1 can vary according to the use to achieve more stability and to deliver more light to the top, respectively.

The rod 1 is cut right-angled at its first end 2. The cut can be ordinarily polished, ground or also polished optically. The second end 3 of the rod comprises the recess 4 into which a tantalum clip may fit. The recess 4 is preferably formed in a U-shape, similar to a feather key groove which is opened towards the second end 3. The bottom of the recess 4 is formed planely so that the tantalum clip can bear on planely. The recess 4 can be formed by pressing or grinding in different ways. If required, the surface in this area can be polished subsequently to achieve maximal transmission. All sharp edges which result from grinding the recess 4, for example, are rounded preferably. This can be accomplished mechanically by polishing or by fire-polishing and by warming the edges and burs.

On the opposite side of the recess 4 the light deflection device 5 is provided which is formed as a prism in this embodiment. Therefore, the rod 1 is slanted at its second end 3. The plane in which the slant is positioned and a plane 4a in which the bottom of the recess is positioned draw an angle and are not tilted to each other. The angle of the prism, i.e. the inner angle between the slant and the perpendicular to the rod axis is selected in such a manner that it ensures a constant lighting of the desired area. The angle of the prism also depends on the length of the recess 4, since the end of the recess directed to the middle of the rod, i.e. the bottom point of the U and the end of the slant which is directed to the middle of the rod preferably are located on the same height referring to the middle of the rod. The angle of the light deflecting device and the angle of the prism, respectively, of approximately 70° has turned out to be optimal. The angle is acute enough to guide the light directly into the eye in a 90° angle referring to the rod axis. If the angle is too acute, the rod is too thick on the top and can not be inserted into the eyehole.

The rod also could be coated completely or partly with blocking filters for wavelengths which are damaging for the eye or could comprise a complete external coating in the form of a vaporization or a coating with a reflecting layer or a plastics or metal jacket 12, to increase the light conduction furthermore, as shown in FIG. 2. Referring to the coating you have to make sure that it is not damaged during the damp sterilization of the rod.

The light feeding device 6 comprises a cold light fiber optic cable 7, a first holder 8, a second holder 9 which are interconnected by a thread 10 in this embodiment. At the junction 11 the light from the cold light fiber optic cable 7 enters the rod 1.

In comparison to state of the art the light does not leave the rod coaxially, but with an angle of 90° to the rod axis. Furthermore, the provided light intensity in the present invention is increased referring to the state of the art.

In operation the rod is put directly on the eye ball after a tantalum clip was sewed. The light which is necessary for the monitoring reaches the rod 1 through the light feeding device 6, is led through the same wherein it is deflected by the light deflecting device in a 90° angle to the rod axis and leaves in the direction of the recess 4. To ensure the irradiation planning and afterwards the exact positioning of the patient during the actual irradiation, the irradiation target volume has to be defined exactly. This is realized by sewing of the radioopaque tantalum clip on the outer surface of the eye. To be able to determine the exact position of the tantalum clip which is sewed on the outer surface of the eye towards the irradiation target volume (tumor), the diaphanoscope rod is put on the tantalum clip by means of its U-shaped recess and the diaphanoscopic shade of the tantalum clip is identified by means of an indirect ophthalmoscopy. Its exact position is marked on a wide angle photograph of the background of the eye referring to the borders of the tumor. The tantalum clips can remain in this position, since they usually cause no complaints and do not constitute an obstacle for other activities.

The invention claimed is:

1. A diaphanoscope rod comprising a rigid rod of a transparent or translucent material, the rod having a first end and a second end, and
a light feeding device, wherein
said second end of the rod comprises a light deflecting device.

2. The diaphanoscope rod according to claim 1, wherein the light deflecting device is a prism.

3. The diaphanoscope rod according to claim 2, wherein the rod comprises a recess at a second end, wherein the recess is formed in such a manner that a tantalum clip fits therein.

4. The diaphanoscope rod according to claim 1, wherein the rod is formed of a material which is drawn out to the predetermined diameter.

5. The diaphanoscope rod according to claim 4, wherein the rod comprises a recess at a second end, wherein the recess is formed in such a manner that a tantalum clip fits therein.

6. The diaphanoscope rod according to claim 1, wherein the rod is cut in a right angle at its first end.

7. The diaphanoscope rod according to claim 6, wherein the rod comprises a recess at a second end, wherein the recess is formed in such a manner that a tantalum clip fits therein.

8. The diaphanoscope rod according to claim 1, wherein the rod comprises a recess at said second end, wherein the recess is formed in such a manner that a tantalum clip fits therein.

9. The diaphanoscope rod according to claim 8, wherein a prism is arranged at said second end at a side of said rod opposite to the recess wherein said prism has a slanted side which is identical to a side of said rod and wherein said slanted side of the prism draws an angle with the perpendicular of the rod axis, the angle being such that a constant lighting of a predetermined area of the eye, the area is to be examined, is ensured.

10. The diaphanoscope rod according to claim 9, wherein the slanted side of the prism draws an angle with the perpendicular of the rod axis of approximately 70°.

11. The diaphanoscope rod according to claim 9, wherein the recess is U-shaped and the bottom of said U-shape faces towards the middle axis of said rod.

12. The diaphanoscope rod according to claim 11, wherein the end of the recess towards the middle of the rod and the end of the slant towards the middle of the rod are arranged in the same height referring to the middle of the rod.

13. The diaphanoscope rod according to claim 1, wherein all sharp edges are rounded.

14. The diaphanoscope rod according to claim 1, wherein the rod is coated with blocking filters for wavelengths which are damaging for the eye.

15. The diaphanoscope rod according to claim 1, wherein the rod is vaporized and/or coated with a reflection layer and/or is covered with a plastics or metal jacket.

* * * * *